(12) United States Patent
Oldenburger et al.

(10) Patent No.: US 11,400,028 B2
(45) Date of Patent: *Aug. 2, 2022

(54) DENTAL MILLING BLANK FOR THE PRODUCTION OF PERMANENT INDIRECT RESTORATIONS AND COMPUTER-AIDED PROCESS FOR PRODUCING THE PERMANENT INDIRECT RESTORATIONS

(71) Applicant: VOCO GmbH, Cuxhaven (DE)

(72) Inventors: Daniel Oldenburger, Cuxhaven (DE); Reinhard Maletz, Cuxhaven (DE); Nils Fontein, Cuxhaven (DE); Manfred Thomas Plaumann, Cuxhaven (DE)

(73) Assignee: VOCO GMBH, Cuxhaven (DE)

( * ) Notice: Subject to any disclaimer, the term of this patent is extended or adjusted under 35 U.S.C. 154(b) by 193 days.

This patent is subject to a terminal disclaimer.

(21) Appl. No.: 16/799,055

(22) Filed: Feb. 24, 2020

(65) Prior Publication Data

US 2020/0188070 A1 Jun. 18, 2020

Related U.S. Application Data

(63) Continuation of application No. 15/897,777, filed on Feb. 15, 2018, now Pat. No. 10,603,143.

(30) Foreign Application Priority Data

Feb. 15, 2017 (DE) .......................... 102017103084.0

(51) Int. Cl.
*A61C 13/00* (2006.01)
*A61C 13/08* (2006.01)
*A61C 19/02* (2006.01)
*A61C 3/00* (2006.01)
*A61K 6/30* (2020.01)
*A61K 6/71* (2020.01)
*A61K 6/887* (2020.01)
*C08F 222/20* (2006.01)
*C08K 3/36* (2006.01)
*C08K 3/40* (2006.01)
*C08K 9/06* (2006.01)

(52) U.S. Cl.
CPC ............... *A61K 6/30* (2020.01); *A61C 3/005* (2013.01); *A61C 13/0004* (2013.01); *A61C 13/0022* (2013.01); *A61C 13/082* (2013.01); *A61C 19/02* (2013.01); *A61K 6/71* (2020.01); *A61K 6/887* (2020.01); *C08K 3/36* (2013.01); *C08K 3/40* (2013.01); *C08K 9/06* (2013.01); *C08K 2201/005* (2013.01); *C08K 2201/011* (2013.01)

(58) Field of Classification Search
CPC . A61C 13/0022; A61C 3/005; A61C 13/0004; A61C 13/082; A61C 19/02; A61K 6/30; A61K 6/887; A61K 6/71; C08F 222/20; C08K 3/36; C08K 3/40; C08K 9/06; C08K 2201/005; C08K 2201/011

USPC ......................................................... 524/494
See application file for complete search history.

(56) References Cited

U.S. PATENT DOCUMENTS

| | | |
|---|---|---|
| 4,002,669 A | 1/1977 | Gross et al. |
| 4,298,738 A | 11/1981 | Lechtken et al. |
| 4,522,693 A | 6/1985 | Henne et al. |
| 4,544,359 A | 10/1985 | Waknine |
| 4,616,073 A | 10/1986 | Antonucci |
| 5,761,169 A | 6/1998 | Mine et al. |
| 5,962,550 A | 10/1999 | Akahane et al. |
| 6,020,528 A | 2/2000 | Leppard et al. |
| 6,030,606 A | 2/2000 | Holmes |
| 6,186,790 B1 | 2/2001 | Karmaker et al. |
| 6,345,984 B2 | 2/2002 | Karmaker et al. |
| 6,403,676 B1 | 6/2002 | Jia et al. |
| 7,081,485 B2 | 7/2006 | Suh et al. |
| 7,148,382 B2 | 12/2006 | Wolf et al. |
| 7,214,726 B2 | 5/2007 | Qian |
| 10,603,143 B2 * | 3/2020 | Oldenburger ........ A61C 13/082 |
| 2006/0247330 A1 | 11/2006 | Takano et al. |
| 2007/0027229 A1 | 2/2007 | Moszner et al. |
| 2014/0050674 A1 | 2/2014 | Tjaderhane |

(Continued)

FOREIGN PATENT DOCUMENTS

| | | |
|---|---|---|
| DE | 1495520 | 4/1969 |
| DE | 2462271 | 9/1976 |
| DE | 102005053775 | 5/2007 |
| DE | 102015220373 | 4/2016 |
| DE | 112006001049 | 4/2017 |
| EP | 0007508 | 2/1980 |
| EP | 0073413 | 3/1983 |
| EP | 0173567 | 5/1986 |
| EP | 0184095 | 6/1986 |

(Continued)

OTHER PUBLICATIONS

Davis, Ed., "Chapter 10: Biomaterials for Dental Applications," Handbook of Material for Medical Devices, ASM International, pp. 214-216. (Year: 2003).

*Primary Examiner* — Josephine L Chang
(74) *Attorney, Agent, or Firm* — Duane Morris LLP; Gregory M. Lefkowitz; Brandon A. Chan

(57) ABSTRACT

A dental milling blank for the production of permanent indirect restorations in the CAD/CAM process, characterized in that it has a water sorption WSP of less than/equal to 18 μg/mm³, measured according to ISO 4049 and an E modulus E greater than/equal to 13 GPa, measured according to the ADA specification No. 27 and a quotient Q of WSP/E of less than 1.35 μg/(GPa×mm³) and consists of the polymerization product of a radically curable dental composition, which comprises
a) inorganic fillers, wherein the total mass of the inorganic fillers is at least 83 wt. %, based on the total mass of the composition,
b) radically polymerizable monomers,
c) one or more initiators for radically curing.

20 Claims, 2 Drawing Sheets

(56) References Cited

U.S. PATENT DOCUMENTS

| | | |
|---|---|---|
| 2014/0162216 A1 | 6/2014 | Craig et al. |
| 2014/0200284 A1 | 7/2014 | Eckert et al. |
| 2014/0220512 A1 | 8/2014 | Abuelyaman et al. |
| 2016/0128812 A1 | 5/2016 | Nakayama et al. |
| 2016/0136059 A1 | 5/2016 | Hecht et al. |

FOREIGN PATENT DOCUMENTS

| | | |
|---|---|---|
| EP | 0206074 | 12/1986 |
| EP | 0209700 | 1/1987 |
| EP | 0254185 | 1/1988 |
| EP | 0262629 | 4/1988 |
| EP | 0366977 | 5/1990 |
| EP | 0948955 | 10/1999 |
| EP | 0980682 | 2/2000 |
| EP | 1112995 | 4/2001 |
| EP | 1236459 | 4/2002 |
| EP | 1839640 | 10/2007 |
| EP | 1872767 | 1/2008 |
| EP | 1881010 | 1/2008 |
| EP | 1935393 | 6/2008 |
| EP | 2055324 | 6/2009 |
| EP | 2070506 | 6/2009 |
| EP | 2070935 | 6/2009 |
| EP | 2623065 | 8/2013 |
| EP | 2881077 | 10/2015 |
| FR | 2226984 | 1/1978 |
| FR | 2640503 | 6/1990 |
| FR | 2645053 | 6/1990 |
| GB | 1209369 | 10/1970 |
| GB | 2259704 | 3/1993 |
| GB | 2325669 | 12/1998 |
| WO | 0040206 | 7/2000 |
| WO | 01/44873 | 6/2001 |
| WO | 02/092021 | 11/2002 |
| WO | 02/092022 | 11/2002 |
| WO | 02/092023 | 11/2002 |
| WO | 2008/049839 | 5/2008 |
| WO | 2011/087832 | 7/2011 |
| WO | 2016/140950 | 9/2016 |

* cited by examiner

SECTION B-B

DENTAL MILLING BLANK FOR THE PRODUCTION OF PERMANENT INDIRECT RESTORATIONS AND COMPUTER-AIDED PROCESS FOR PRODUCING THE PERMANENT INDIRECT RESTORATIONS

CROSS-REFERENCE TO RELATED APPLICATIONS

This application is a continuation of U.S. application Ser. No. 15/897,777, filed Feb. 15, 2018, which claims priority to German Application No. 10 2017 103084.0 filed Feb. 15, 2017, the entireties of which are incorporated herein by reference.

The present invention relates to dental milling blanks based on plastic, so-called composite blocks, for the production of dental prostheses in a CAD/CAM process. Prosthetic restorations form a replacement for teeth and for example include crowns and bridges, partial crowns, inlays, onlays or veneers.

Technical progress with computer-controlled machines has been attended by the development of milling machines which, in a very short time and at minimal cost, are capable of producing prosthetic restorations with unheard-of precision. Against this background, so-called "digital dentistry" has developed. Today it is of outstanding importance in dental technology.

Initially, only ceramic or metallic materials were milled, however, as the dental composite materials became ever better matched to the hard tooth tissue, this substance class also became of interest for use as a milling blank.

Unlike composite materials, which by specific formulation of resin matrix and filler composition can be adapted to the manifold requirements for a dental material in the hostile environment of the oral cavity, ceramic materials can have too high a degree of hardness and because of their inherent brittleness have a tendency to fracture. Metallic materials are poorly acceptable for aesthetic reasons, and often cause allergic reactions in patients.

The present invention relates to a high performance composite block for the production of permanent indirect restorations in the CAD/CAM process. A dental composite material is understood by those skilled in the art to be a radically polymerizable or radically polymerized composition which contains at least one radically polymerizable liquid or one radically polymerized solid resin phase, a solid phase, comprising fillers in a great diversity of types and quantities, one or more polymerization initiator(s) and optionally common additives such as inhibitors, dyes, stabilizers, etc. The not yet radically-cured composite material can be radically polymerized either chemically and/or thermally and/or photochemically by irradiation.

Dental composite blocks, or dental milling blanks, are known from the prior art.

DE 699 22 413 T2 describes a cuttable blank which contains a polymer resin and a finely divided filler material with a maximum particle diameter of less than 50 micrometers. The resin phase of the dental compositions studied in this document comprises the system bis-GMA (2,2-bis[4-(2-hydroxy-3-methacryloyloxypropoxy)phenyl]propane)/TEGDMA (triethylene glycol dimethacrylate), the filler phase contains surface-silanized silicic acid and glass.

EP 3 050 533 A1 discloses dental resin blocks which use as the resin phase UDMA/TEGDMA (urethane dimethacrylate/triethylene glycol dimethacrylate) 80/20, UDMA/bis-MEPP/HDP (urethane dimethacrylate/2,2-bis(4-methacryloxypolyethoxyphenyl)propane/2-hydroxy-1,3-dimethacryloxypropane 60/20/20 and 50/30/20 and UDMA/bis-MEPP (urethane dimethacrylate/2,2-bis(4-methacryloxypolyethoxyphenyl)propane 60/40. Unfortunately it is not clear from the document which urethane dimethacrylate is used. According to an older examined and published application (DE 26 56 847) by the same applicant, the degree of ethoxylation of the bis-MEPP lies in the range from 2.2 to 6. This means that for the production of the bis-MEPP the bisphenol A is reacted with 2.2 to 6 moles of ethylene oxide and finally this intermediate product is saturated with 2 moles of methacrylic acid. These resin compositions are mixed with inorganic fillers to give radically curable pastes in filler to resin weight ratios from 64:36 to 70.8:29.2 and then thermally polymerized to resin blocks by means of BPO (benzoyl peroxide).

DE 24 62 271 C2 claims dental molded bodies containing at least one polymerized acrylate or methacrylate and a silanized microfine inorganic filler based on silicon dioxide, which are characterized in that as the polymerized acrylate or methacrylate they contain a polymerization product of bis-GMA or another derivative of bisphenol A or a reaction product from hydroxyethyl methacrylates and diisocyanates, optionally together with polymerization products of short-chain methacrylate esters and/or bifunctional acrylate or methacrylate esters and as the inorganic filler exclusively microfine silicon dioxide with a particle size from 10 to 400 nm and with a BET surface area of less than 200 $m^2/g$ in a quantity from 20 to 80%, based on the weight of the material. The quantity of the microfine silicic acid can lie in the range between 40 to 75 weight percent, based on the molded bodies.

EP 2 623 065 B1 discloses blanks for a dental mill which target high mechanical properties such as flexural strength and gloss stability. These properties are achieved by means of a blank for a dental mill which is formed from a cured product from a curable composition and comprises: (a) a polymerizable monomer; (b) a spherical inorganic filler which has an average primary particle size of not less than 0.1 μm and less than 1 μm and (c) an inorganic ultrafine particle aggregate filler, consisting of aggregates of inorganic ultrafine particles which have an average primary particle size from 2 to 50 nm. As the resin matrix, a monomer mixture of bis-GMA/TEGDMA/bis-MEPP (2,2-bis[4-(2-hydroxy-3-methacryloyloxypropoxy)-phenyl]propaney (triethylene glycol dimethacrylate)/2,2-bis(4-methacryloxypolyethoxy-phenyl)propane in the weight ratio 20/30/50 is used here.

WO 2011/087832 A1 relates to thermally cured composite blanks which should have significantly improved mechanical and esthetic properties. The radically curable compositions contain initiators which thermally decompose. Since the decomposition takes place at higher temperatures, monomers are prevented from gelling prematurely under normal processing conditions and discoloring the blank because of degradation processes.

WO 2016/140950 A1 describes composite materials which in the cured state can also be used as dental milling blanks. The compositions contain a curable resin component, ceramic fibers and filler in the form of nanoclusters. The polymers should yield highly esthetic restorations and have excellent polishability and polish retention properties. In a practical example, the composition of a resin phase is stated, whose components bis-GMA, TEGDMA, UDMA, bisEMA-6 (ethoxylated bisphenol A dimethacrylate with 6 ethoxy groups) and PEG600DM (polyethylene glycol dimethacrylate with a molecular weight of the polyethylene units of ca. 600 g/mol) is used in weight ratios of 25/1.2/35/35/3.8.

EP 2 881 077 A1 relates to milling blanks which should have excellent mechanical properties, excellent abrasion resistance and excellent surface gloss. Here, these properties are to be achieved via process technology. In contrast to the conventional production methods, in which the composite material is processed by homogeneous mixing and kneading of a curable monomer mixture with a filler into a paste which must have a certain flowability in order to be cured to a milling blank in a mold, this application proposes hot-pressing the inorganic filler in order to aggregate it and finally infiltrating it with the curable resin. The resin should thus fill the interstitial spaces of the primary particles and can then be cured. This process should allow the production of blanks in which the filler particles lie closer to one another than is possible in the conventional production process and thus make it possible to provide milling blanks with a particularly high filler content.

U.S. Pat. No. 6,345,984 B2 relates to milling blanks wherein the composite material contains a particulate filler in a size range from about 0.1 to 5.0 µm and colloidal silicate at a size of 1 to about 70 nm and a resin phase of ethoxylated BPA (bisphenol A) dimethacrylate and the degree of ethoxylation ranges from 1 to 20, preferably from 2 to 7 moles ethylene oxide/mole BPA. The milling blank overall consists of ca. 20 to ca. 30 wt. % of an organic matrix and ca. 65 to ca. 85 wt. % particulate filler, wherein the organic matrix consists of ca. 65 to ca. 90 wt. % ethoxylated BPA dimethacrylate and of ca. 10 to ca. 30 wt. % of a methacrylate oligomer, for example a polycarbonate dimethacrylate condensation product. Taking account of U.S. Pat. No. 4,544,359, cited in U.S. Pat. No. 6,345,984 B2, this typical composition of a milling blank then appears as follows: particulate filler (0.1 to 5 µm) 65 to 79 wt. %, colloidal silicate (1 to 70 nm) 1 to 5 wt. % and organic matrix 20 to 30 wt. %.

U.S. Pat. No. 6,186,790 shows finished dental bridge elements, wherein the composite material is fiber-reinforced.

DE 198 23 530 B4 relates to a dental resin material which is shaped into a dental prosthesis by milling, which comprises an acrylic resin polymer which contains 20 to 70 wt. % of an inorganic filler with an average particle size from 10 to 40 nm in diameter, 1 to 40 wt. % of a glass powder with an average particle size from 0.1-5 µm in diameter and 1-40 wt. % of an organic-inorganic composite filler, which is produced by mixing and curing a mixture of an ultrafine inorganic filler with an average particle size from 10 to 40 nm in diameter and a methacrylate or acrylate monomer with at least one unsaturated double bond and pulverizing the cured mixture such that it has an average particle size from 5 to 50 µm in diameter, wherein the acrylic resin polymer comprises a combination of a methacrylate or acrylate monomer with at least one unsaturated double bond and a thermal polymerization initiator. In example 5, the composite composition of a milling blank is described. The resin phase comprises UDMA/bis-MEPP in a weight ratio of 5/20 and the solid phase contains 22 wt. % inorganic filler (for example Aerosil with an average particle size from 10 to 40 nm), for example OX-50 (with 40 nm primary particle size), 23 wt. % quartz glass powder (average particle size: 0.5 µm) and 30 wt. % barium glass powder (average particle size: 0.5 µm).

DE 601 11 868 T2 claims dental composites for making crowns, coatings, direct fillings, inlays, onlays and splints. The dental compositions contain a polymerizable resin and 11 to 80 vol. % filler, which essentially consists of a ground structural filler and a nanofiller, wherein the ground structural filler makes up between 10 vol. % and 70 vol. % of the composite and consists of ground particles with an average particle size between 0.05 and 0.5 µm and wherein the ground structural filler contains less than 50 vol. % of particles over 0.5 µm in diameter and wherein the nanofiller makes up between 1.0 and 15 vol. % of the composite and essentially consists of discrete, non-aggregated particles with an average particle size of less than 100 nm. In the examples, the total filler content in wt. % lies between 75 and 82.4 wt. %. Resin 1 comprises bis-GMA/TEGDMA and ethoxylated BPA dimethacrylate with 3.5 ethoxy groups per molecule in the weight ratio 3.0/25/72. Resin 2 contains ethoxylated BPA dimethacrylate with 2.0 ethoxy groups per molecule and HEDMA in the weight ratio 90/10.

In U.S. Pat. No. 5,962,550, a resin-modified glass ionomer cement is disclosed as a direct filling material, as core build-up material and as a sealing material for pits and fissures. Within the experimental binder compositions studied, this system inter alia contains the following parts by weight in the resin phase: bis-MEPP/UDMA/HEMA (hydroxyethyl methacrylate) 45/45/10, bis-MEPP/UDMA/BG (butanediol dimethacrylate) 45/45/10, bis-MEPP/UDMA/TEGDMA 33/38/29, and bis-MEPP/UDMA/HEMA 20/46/34.

U.S. Pat. No. 4,616,073 describes highly fluorinated methacrylate prepolymers which are used in non-hydroxylated bis-GMA systems and should be suitable for use as sealing material and cement. These hydrophobic compositions should as far as possible not be sensitive to chemical softening or chemical degradation. Furthermore, they should exhibit little polymerization shrinkage and low water sorption. In the examples, there are filler-free compositions in which the bis-EMA (2,2-bis[(methacryloxyethyloxy)phenyl]propane) with 2 ethoxy groups is used together with DMDMA (1,10-decamethylene dimethacrylate), PDFOMA (pentadecafluorooctyl methacrylate) and BDMA (p-tert.-butyl-N,N-dimethylaniline) in weight ratios 44.31/44.31/11.15/0.23 and 44.25/44.25/11.15/0.35 and 49.25/41.25/9.30/0.20 and 45.91/45.91/7.98/0.20. In the filler-containing compositions, the bis-EMA is used in quantities of 10 and 5.8 wt. % (mold No. 5 and 10B).

Inter alia, U.S. Pat. No. 6,030,606 also relates to cured products such as crowns, bridges, inlays, onlays and implants. The compositions according to the invention, which should have an excellent property profile such as high material strength and hardness, contain 10-30% of a resin component, which comprises:

15 to 45% bisEMA6, 15 to 45% UDMA, 10 to 40% bis-GMA and 0 to 10% TEGDMA. The number of ethoxy groups in the bisEMA6 should lie between 5 and 8, preferably about 6.

DE 10 2015 220 373 A1 discloses both curable and also cured dental materials and also claims milling blanks. The compositions described here comprise a bimodal glass composition.

In the prior art concerning milling blanks, work is targeted above all on the mechanical properties such as flexural strength and hardness and on the esthetic aspects of the blanks.

In spite of major advances in materials development, increasingly greater demands are being made on modern dental restorative materials. This applies to both the direct filling materials and also indirect materials such as for example CAD/CAM-produced restorations. In addition to increasing esthetic demands for example in terms of color, translucency/opacity and opalescence of the milling blanks, there are also more stringent requirements regarding the physical properties. Thus inter alia the materials should have high strength, low abrasion, good X-ray opacity and low water sorption.

The water sorption in particular can lead to a great variety of problems. Thus, as a rule, in case of high water sorption, increased discolorations occur, since colored substances are often also absorbed with the water. Apart from this esthetic aspect, however, as a result of increased water sorption the ester bonds of the radically cured resin matrix may be hydrolytically cleaved and thus mechanical parameters such as strength and abrasion resistance be reduced.

The stress arising in the material is generally described by the stress tensor ($\sigma_{ij}$) and the resulting deformation by the strain tensor ($\varepsilon_{kl}$). Both are second order tensors.

$$\sigma_{ij} = \begin{bmatrix} \sigma_{11} & \sigma_{12} & \sigma_{13} \\ \sigma_{21} & \sigma_{22} & \sigma_{23} \\ \sigma_{31} & \sigma_{32} & \sigma_{33} \end{bmatrix} \varepsilon_{kl} = \begin{bmatrix} \varepsilon_{11} & \varepsilon_{12} & \varepsilon_{13} \\ \varepsilon_{21} & \varepsilon_{22} & \varepsilon_{23} \\ \varepsilon_{31} & \varepsilon_{32} & \varepsilon_{33} \end{bmatrix} \quad (1)$$

The stress tensor is combined with the strain tensor via the elasticity tensor ($E_{ijkl}$), wherein the elasticity tensor is a fourth order tensor with 81 components (i,j,k,l=1, ..., 3).

$$\sigma_{ij} = E_{ijkl}\varepsilon_{kl} \quad (2)$$

However, due to the symmetry of stress and strain tensor, the number of the independent components of $E_{ijkl}$ after transformation into $E_{IJ}$ decreases to 36. Thus the elasticity constant can be represented in a 6×6 matrix and the stress and the strain each as six-component vectors.

$$\begin{bmatrix} \sigma_1 \\ \sigma_2 \\ \sigma_3 \\ \sigma_4 \\ \sigma_5 \\ \sigma_6 \end{bmatrix} = \begin{bmatrix} E_{11} & E_{12} & E_{13} & E_{14} & E_{15} & E_{16} \\ E_{21} & E_{22} & E_{23} & E_{24} & E_{25} & E_{26} \\ E_{31} & E_{32} & E_{33} & E_{34} & E_{35} & E_{36} \\ E_{41} & E_{42} & E_{43} & E_{44} & E_{45} & E_{46} \\ E_{51} & E_{52} & E_{53} & E_{54} & E_{55} & E_{56} \\ E_{61} & E_{62} & E_{63} & E_{64} & E_{65} & E_{66} \end{bmatrix} \begin{bmatrix} \varepsilon_1 \\ \varepsilon_2 \\ \varepsilon_3 \\ \varepsilon_4 \\ \varepsilon_5 \\ \varepsilon_6 \end{bmatrix} \quad (3)$$

Thus, in simple terms, the relationship between the stress ($\sigma$) arising from water sorption and the resulting deformation $\varepsilon$ (swelling) emerges via the elastic modulus (E) as a proportionality constant:

$$\sigma = E\varepsilon \text{ or} \quad (4)$$

$$\varepsilon = \frac{\sigma}{E} \quad (5)$$

From this it emerges that a material with a high elastic modulus is better able to counteract stresses occurring, so that with the same stress a smaller deformation results.

It has now been found that for cured dental composites the deformation (swelling) occurring is proportional to the water sorption ($W_{SP}$) and moreover inversely proportional to the elastic modulus. This means that the stress occurring is proportional to the water sorption.

$$\varepsilon \sim \sigma \sim W_{SP} \text{ and} \quad (6)$$

$$\varepsilon \sim \frac{1}{E} \quad (7)$$

$$\varepsilon \sim \frac{W_{SP}}{E} \quad (8)$$

Figure 1:
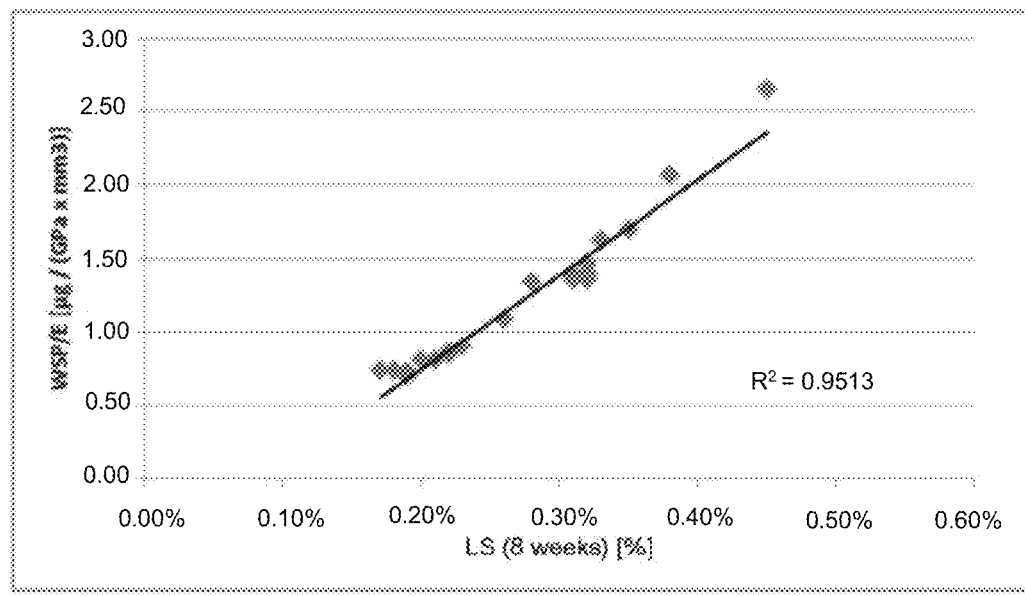
FIG. 1 shows the diagram of the quotient of water sorption/elastic modulus against the linear swelling for experimental milling blanks.
Figure 2:
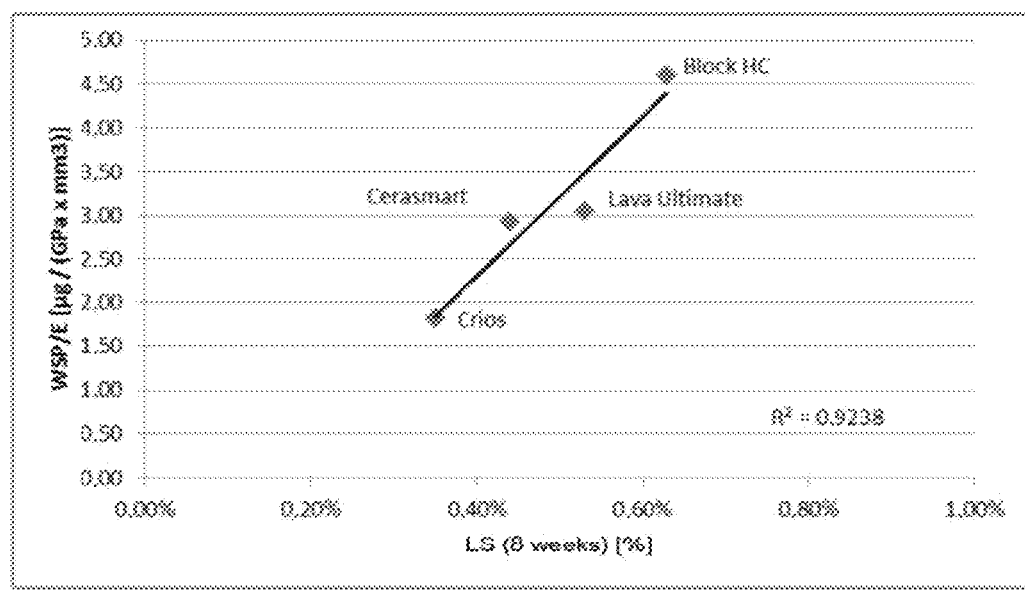
FIG. 2 shows the diagram of the quotient of water sorption/elastic modulus against the linear swelling for commercial milling blanks.

From FIGS. 1 and 2, a good correlation emerges between this quotient and the linear swelling. The data from these diagrams derive from the examples (see experimental section).

In particular, it is surprising that the proportionality exists not simply between the swelling and the water sorption, but rather between the swelling and the quotient of water sorption and elastic modulus. Thus, with equal water sorption, materials with different elastic moduli display different degrees of swelling.

However, the above finding of a strict proportionality between water sorption and swelling (with constant E modulus) is itself surprising, in that the phenomenon here discovered for the first time cannot be explained solely by the volume of the absorbed water molecules in the polymer, since analogous experiments with organic solvents instead of water showed no proportionality between their sorption and swelling of the material. Presumably, the water molecules have a destructive effect on existing superstructures such as the secondary or tertiary structure in the polymer. Under the extreme conditions in the oral environment, particularly under the constant influence of saliva, water sorption by the finished restoration takes place. Water molecules embed themselves in the polymer network, form hydrogen bridge bonds there, claim space for themselves and disturb established superstructures. This results in stresses in the material. On the microscopic scale, broadening of the polymer network, and on the macroscopic scale swelling of the restoration results.

For example, the swelling of a crown leads to an increase in the external and internal diameter, since the whole restoration expands due to the swelling. Here the relative linear swelling (in percent) is about one third of the relative volume swelling (in percent). By increasing the internal diameter, a tensile force arises, which is exerted on the adhesive bond of the luted crown. If the tensile forces locally exceed the adhesion, breaking away of the luting material and marginal gap formation results. These sites involve an increased risk of colonization by bacteria and the formation of secondary caries. If the swelling is large enough or the continuing loading of the defect sites formed is high enough, total loss of retention of the restoration occurs.

Restorations produced from composite milling blanks are adhesively luted. During this, the stresses arising due to the swelling are transferred via the luting composite onto the adhesive bond to the tooth substance. Typical adhesive luting composites have elastic moduli of about 5 GPa (Journal of Prosthodontic Research 2010, 54, 59-64). Thus in case of a swelling of more than 0.25%, tensile stresses of more than 12.5 MPa act on the adhesive bond. In case of swelling of more than 0.3%, tensile stresses of more than 15

MPa operate. In case of higher swelling and higher tensile stresses associated therewith, the bond strengths of the luting material are exceeded and loss of retention occurs.

In order to be able to provide securely retained and marginal gap-free prosthetic restorations, it was thus the objective of the invention to obtain (as far as possible) swelling-free milling blanks.

In our own extensive studies, we were able to show that these materials are accessible when their water sorption WSP is less than/equal to 18 µg/mm$^3$, measured according to ISO 4049 and their E modulus E greater than/equal to 13 GPa, measured according to the ADA specification No. 27 and the quotient Q of WSP/E less than 1.35 µg/(GPa×mm$^3$), preferably when their water sorption WSP is less than/equal to 15 µg/mm$^3$, measured according to ISO 4049 and their E modulus E greater than/equal to 15 GPa, measured according to the ADA specification No. 27 and the quotient Q of WSP/E less than 1 µg/(GPa×mm$^3$).

Dental milling blanks with the values stated above were hitherto unknown in the prior art (see Table 1 and FIG. 2).

Entirely surprisingly, we further found that the above conditions for obtaining (as far as possible) swelling-free or only minimally swelling polymers can be achieved when the proportion by weight of ethoxylated bisphenol-A dimethacrylate with an average degree of ethoxylation of 2 to 4 ethoxy groups per molecule is greater than 40 weight percent and less than 50 weight percent of the quantity of radically polymerizable monomers used and the total mass of inorganic fillers makes up at least 83 weight percent of the total composition. This finding was not to be expected since with a proven hydrophobic monomer such as HDDMA (hexanediol dimethacrylate) the above values for the water sorption could not be achieved. Those skilled in the art would have expected that due to the higher polarity of the ethoxy bond and the aromatic character of the BPA ring structure, actually a higher water sorption would have to take place compared to a purely aliphatic hydrocarbon skeleton such as that of HDDMA, which is however not the case.

The present invention thus relates to a high performance composite block, more specifically a dental milling blank for the production of permanent indirect restorations in the CAD/CAM process, which is characterized in that it has a water sorption WSP of less than/equal to 18 µg/mm$^3$, measured according to ISO 4049 and an E modulus E greater than/equal to 13 GPa, measured according to the ADA specification No. 27 and a quotient Q of WSP/E of less than 1.35 µg/(GPa×mm$^3$), preferably has a water sorption WSP of less than/equal to 15 µg/mm$^3$, measured according to ISO 4049 and an E modulus E greater than/equal to 15 GPa, measured according to the ADA specification No. 27 and a quotient Q of WSP/E of less than 1 µg/(GPa×mm$^3$) and which consists of the polymerization product of a radically curable dental composition, which comprises
  a) inorganic fillers, wherein the total mass of the inorganic fillers is at least 83 wt. %, based on the total mass of the composition,
  b) radically polymerizable monomers,
  c) one or more initiators for radical curing and
  d) optionally additives.

A preferred dental milling blank for the production of permanent indirect restorations in the CAD/CAM process which is characterized in that it has a water sorption WSP of less than/equal to 18 µg/mm$^3$, measured according to ISO 4049 and an E modulus E greater than/equal to 13 GPa, measured according to the ADA specification No. 27 and a quotient Q of WSP/E of less than 1.35 µg/(GPa×mm$^3$), preferably has a water sorption WSP of less than/equal to 15 µg/mm$^3$, measured according to ISO 4049 and an E modulus E greater than/equal to 15 GPa, measured according to the ADA specification No. 27 and a quotient Q of WSP/E of less than 1 µg/(GPa×mm$^3$) and which consists of the polymerization product of a radically curable dental composition, which comprises
  a) inorganic fillers, wherein the total mass of the inorganic fillers is at least 83 wt. %, based on the total mass of the composition,
  b) radically polymerizable monomers, which comprise bifunctional (meth)acrylates, wherein the proportion by weight of ethoxylated bisphenol-A dimethacrylate with an average degree of ethoxylation of 2 to 4 ethoxy groups per molecule is greater than 40% wt. % and less than 50 wt. % of b),
  c) one or more initiators for radically curing and
  d) optionally additives.

A further preferred milling blank for the production of permanent indirect restorations in the CAD/CAM process is characterized in that it has a water sorption WSP of less than/equal to 18 µg/mm$^3$, measured according to ISO 4049 and an E modulus E greater than/equal to 13 GPa, measured according to the ADA specification No. 27 and a quotient Q of WSP/E of less than 1.35 µg/(GPa×mm$^3$), preferably has a water sorption WSP of less than/equal to 15 µg/mm$^3$, measured according to ISO 4049 and an E modulus E greater than/equal to 15 GPa, measured according to the ADA specification No. 27 and a quotient Q of WSP/E of less than 1 µg/(GPa×mm$^3$) and which consists of the polymerization product of a radically curable dental composition, which comprises
  a) inorganic fillers, wherein the total mass of the inorganic fillers is at least 83 wt. %, based on the total mass of the composition, and wherein the inorganic fillers a) comprise,
    a1) a glass composition and
    a2) non-aggregated and non-agglomerated silicic acid with an average particle size of not more than 80 nm and
  b) radically polymerizable monomers, which comprise bifunctional (meth)acrylates, wherein the proportion by weight of ethoxylated bisphenol-A dimethacrylate with an average degree of ethoxylation of 2 to 4 ethoxy groups per molecule is greater than 40% wt. % and less than 50 wt. % of b) and
  c) one or more initiators for radically curing and
  d) optionally additives.

A quite preferred milling blank for the production of permanent indirect restorations in the CAD/CAM process is characterized in that it has a water sorption WSP of less than/equal to 18 µg/mm$^3$, measured according to ISO 4049 and an E modulus E greater than/equal to 13 GPa, measured according to the ADA specification No. 27 and a quotient Q of WSP/E of less than 1.35 µg/(GPa×mm$^3$), preferably has a water sorption WSP of less than/equal to 15 µg/mm$^3$, measured according to ISO 4049 and an E modulus E greater than/equal to 15 GPa, measured according to the ADA specification No. 27 and a quotient Q of WSP/E of less than 1 µg/(GPa×mm$^3$) and which consists of the polymerization product of a radically curable dental composition, which comprises
  a) inorganic fillers, wherein the total mass of the inorganic fillers is at least 83 wt. %, based on the total mass of the composition, and wherein the inorganic fillers a) comprise,
    a1) a glass composition and
    a2) non-aggregated and non-agglomerated silicic acid with an average particle size of not more than 80 nm, wherein the glass composition a1) comprises a first glass composition a1a) with a D50 value from 0.4-1.0 µm, preferably from 0.5-0.9 µm, and a second glass composition a1b) with a D50 value from 1.2-5.0 µm, preferably from 1.5-4.0 µm, and wherein the mass ratio of a1a) to a1b) lies between 1:1.5 and 1:8, preferably between 1:2 to 1:5 and the mass ratio of a2) to the sum of a1a) and a1b) lies between 1:3 and 1:6 and the ratio of the average particle size of the first microparticle fraction a1a) to the average particle size of the second microparticle fraction a1b) lies in the range from 1:1.5 to 1:10, preferably 1:2 to 1:5, wherein the D75 value of a1a) is smaller than the D25 value of a1b) and b) radically polymerizable monomers, which comprise bifunctional (meth)acrylates, wherein the proportion by weight of ethoxylated bisphenol-A dimethacrylate with an average degree of ethoxylation of 2 to 4 ethoxy groups per molecule is greater than 40% wt. % and less than 50 wt. % of b) and c) one or more initiators for radically curing and d) optionally additives.

A particularly preferred milling blank for the production of permanent indirect restorations in the CAD/CAM process is characterized in that it has a water sorption WSP of less than/equal to 18 µg/mm³, measured according to ISO 4049 and an E modulus E greater than/equal to 13 GPa, measured according to the ADA specification No. 27 and a quotient Q of WSP/E of less than 1.35 µg/(GPa×mm³), preferably has a water sorption WSP of less than/equal to 15 µg/mm³, measured according to ISO 4049 and an E modulus E greater than/equal to 15 GPa, measured according to the ADA specification No. 27 and a quotient Q of WSP/E of less than 1 µg/(GPa×mm³) and which consists of the polymerization product of a radically curable dental composition, which comprises a) inorganic fillers, wherein the total mass of the inorganic fillers is at least 83 wt. %, based on the total mass of the composition, and wherein the inorganic fillers a) comprise, a1) a glass composition and a2) non-aggregated and non-agglomerated silicic acid with an average particle size of not more than 80 nm, wherein the glass composition comprises a1) a first glass composition a1a) with a D50 value from 0.4-1.0 µm, preferably from 0.5-0.9 µm, and a second glass composition a1b) with a D50 value from 1.2-5.0 µm, preferably from 1.5-4.0 µm, and wherein the mass ratio of a1a) to a1b) lies between 1:1.5 and 1:8, preferably between 1:2 to 1:5 and the mass ratio of a2) to the sum of a1a) and a1b) lies between 1:3 and 1:6 and the ratio of the average particle size of the first microparticle fraction a1a) to the average particle size of the second microparticle fraction a1b) lies in the range from 1:1.5 to 1:10, preferably 1:2 to 1:5, wherein the D75 value of a1a) is smaller than the D25 value of a1b) and wherein the proportion of the non-aggregated and non-agglomerated silicic acid with an average particle size of not more than 80 nm a2) is greater than 11.86 wt. % and less than 23 wt. %, based on the total composition, and b) radically polymerizable monomers, which comprise bifunctional (meth)acrylates, wherein the proportion by weight of ethoxylated bisphenol-A dimethacrylate with an average degree of ethoxylation of 2 to 4 ethoxy groups per molecule is greater than 40% wt. % and less than 50 wt. % of b), wherein the quantity of radically polymerizable monomers b) lies in a quantity range of at most 16.7 wt. %, based on the total composition, and c) one or more initiators for radically curing from 0.2 to 5 wt. %, based on the total composition, and d) additives in a quantity range from 0.001 wt. % to 2 wt. %, based on the total composition.

In other words, the present invention thus relates to a dental milling blank for the production of permanent indirect restorations in the CAD/CAM process, which is characterized in that it has a water sorption WSP of less than/equal to 18 µg/mm³, measured according to ISO 4049 and an E modulus E greater than/equal to 13 GPa, measured according to the ADA specification No. 27 and a quotient Q of WSP/E of less than 1.35 µg/(GPa×mm³), preferably has a water sorption WSP of less than/equal to 15 µg/mm³, measured according to ISO 4049 and an E modulus E greater than/equal to 15 GPa, measured according to the ADA specification No. 27 and a quotient Q of WSP/E of less than 1 µg/(GPa×mm³) and which contains a) inorganic fillers, wherein the total mass of the inorganic fillers is least 83 wt. %, based on the total mass of the milling blank, and b) polymerized fractions of radically polymerizable monomers.

In other words, the present invention thus relates to a preferred dental milling blank for the production of permanent indirect restorations in the CAD/CAM process, which is characterized in that it has a water sorption WSP of less than/equal to 18 µg/mm³, measured according to ISO 4049 and an E modulus E greater than/equal to 13 GPa, measured according to the ADA specification No. 27 and a quotient Q of WSP/E of less than 1.35 µg/(GPa×mm³), preferably has a water sorption WSP of less than/equal to 15 µg/mm³, measured according to ISO 4049 and an E modulus E greater than/equal to 15 GPa, measured according to the ADA specification No. 27 and a quotient Q of WSP/E of less than 1 µg/(GPa×mm³) and which contains a) inorganic fillers, wherein the total mass of the inorganic fillers is at least 83 wt. %, based on the total mass of the milling blank, and b) polymerized fractions of radically polymerizable monomers, which comprise bifunctional (meth)acrylates, wherein the proportion by weight of polymerized ethoxylated bisphenol-A dimethacrylate with an average degree of ethoxylation of 2 to 4 ethoxy groups per molecule is greater than 40% wt. % and less than 50 wt. % of b).

In other words, the present invention thus relates to a further preferred milling blank for the production of permanent indirect restorations in the CAD/CAM process, which is characterized in that it has a water sorption WSP of less than/equal to 18 µg/mm³, measured according to ISO 4049 and an E modulus E greater than/equal to 13 GPa, measured according to the ADA specification No. 27 and a quotient Q of WSP/E of less than 1.35 µg/(GPa×mm³), preferably has a water sorption WSP of less than/equal to 15 µg/mm³, measured according to ISO 4049 and an E modulus E greater than/equal to 15 GPa, measured according to the ADA specification No. 27 and a quotient Q of WSP/E of less than 1 µg/(GPa×mm³) and contains a) inorganic fillers, wherein the total mass of the inorganic fillers is at least 83 wt. %, based on the total mass of the milling blank, and wherein the inorganic fillers a) comprise, a1) a glass composition and a2) non-aggregated and non-agglomerated silicic acid with an average particle size of not more than 80 nm and b) polymerized fractions of radically polymerizable monomers, which comprise bifunctional (meth)acrylates, wherein the proportion by weight of ethoxylated bisphenol-A dimethacrylate with an average degree of ethoxylation of 2 to 4 ethoxy groups per molecule is greater than 40% wt. % and less than 50 wt. % of b).

In other words, the present invention thus relates to a quite preferred milling blank for the production of permanent indirect restorations in the CAD/CAM process, which is characterized in that it has a water sorption WSP of less than/equal to 18 µg/mm$^3$, measured according to ISO 4049 and an E modulus E greater than/equal to 13 GPa, measured according to the ADA specification No. 27 and a quotient Q of WSP/E of less than 1.35 µg/(GPa×mm$^3$), preferably has a water sorption WSP of less than/equal to 15 µg/mm$^3$, measured according to ISO 4049 and an E modulus E greater than/equal to 15 GPa, measured according to the ADA specification No. 27 and a quotient Q of WSP/E of less than 1 µg/(GPa×mm$^3$) and which contains a) inorganic fillers, wherein the total mass of the inorganic fillers is at least 83 wt. %, based on the total mass of the milling blank, and wherein the inorganic fillers a) comprise, a1) a glass composition and a2) non-aggregated and non-agglomerated silicic acid with an average particle size of not more than 80 nm, wherein the glass composition a1) comprises a first glass composition a1a) with a D50 value from 0.4-1.0 µm, preferably from 0.5-0.9 µm, and a second glass composition a1b) with a D50 value from 1.2-5.0 µm, preferably from 1.5-4.0 µm, and wherein the mass ratio of a1a) to a1b) lies between 1:1.5 and 1:8, preferably between 1:2 to 1:5 and the mass ratio of a2) to the sum of a1a) and a1b) lies between 1:3 and 1:6 and the ratio of the average particle size of the first microparticle fraction a1a) to the average particle size of the second microparticle fraction a1b) lies in the range from 1:1.5 to 1:10, preferably 1:2 to 1:5, wherein the D75 value of a1a) is smaller than the D25 value of a1b) and b) polymerized fractions of radically polymerizable monomers, which comprise bifunctional (meth)acrylates, wherein the proportion by weight of ethoxylated bisphenol-A dimethacrylate with an average degree of ethoxylation of 2 to 4 ethoxy groups per molecule is greater than 40% wt. % and less than 50 wt. % of b).

In other words, the present invention thus relates to a particularly preferred milling blank for the production of permanent indirect restorations in the CAD/CAM process, which is characterized in that it has a water sorption WSP of less than/equal to 18 µg/mm$^3$, measured according to ISO 4049 and an E modulus E greater than/equal to 13 GPa, measured according to the ADA specification No. 27 and a quotient Q of WSP/E of less than 1.35 µg/(GPa×mm$^3$), preferably has a water sorption WSP of less than/equal to 15 µg/mm$^3$, measured according to ISO 4049 and an E modulus E greater than/equal to 15 GPa, measured according to the ADA specification No. 27 and a quotient Q of WSP/E of less than 1 µg/(GPa×mm$^3$) and which contains a) inorganic fillers, wherein the total mass of the inorganic fillers is at least 83 wt. %, based on the total mass of the milling blank, and wherein the inorganic fillers a) comprise, a1) a glass composition and a2) non-aggregated and non-agglomerated silicic acid with an average particle size of not more than 80 nm, wherein the glass composition a1) comprises a first glass composition a1a) with a D50 value from 0.4-1.0 µm, preferably from 0.5-0.9 µm, and a second glass composition a1b) with a D50 value from 1.2-5.0 µm, preferably from 1.5-4.0 µm, and wherein the mass ratio of a1a) to a1b) lies between 1:1.5 and 1:8, preferably between 1:2 to 1:5 and the mass ratio of a2) to the sum of a1a) and a1b) lies between 1:3 and 1:6 and the ratio of the average particle size of the first microparticle fraction a1a) to the average particle size of the second microparticle fraction a1b) lies in the range from 1:1.5 to 1:10, preferably 1:2 to 1:5, wherein the D75 value of a1a) is smaller than the D25 value of a1b) and wherein the proportion of the non-aggregated and non-agglomerated silicic acid with an average particle size of not more than 80 nm a2) is greater than 11.86 wt. % and less than 23 wt. %, based on the total composition, b) polymerized fractions of radically polymerizable monomers, which comprise bifunctional (meth)acrylates, wherein the proportion by weight of ethoxylated bisphenol-A dimethacrylate with an average degree of ethoxylation of 2 to 4 ethoxy groups per molecule is greater than 40% wt. % and less than 50 wt. % of b), wherein the quantity of radically polymerizable monomers b) lies in a quantity range of at most 16.7 wt. %, based on the total composition.

a) Inorganic Fillers

The milling blank according to the invention comprises inorganic fillers in a quantity of at least 83 wt. %, based on the total composition. The inorganic fillers are preferably used as mixtures. To optimize the product properties, the inorganic fillers are incorporated into the compositions in different particle sizes, wherein they preferably have a multimodal, quite preferably a bimodal distribution.

As inorganic fillers, compact glasses and various silicic acids in various sizes and states (monodisperse, polydisperse) can be used.

Suitable inorganic components are for example amorphous materials based on mixed oxides made up of $SiO_2$, $ZrO_2$ and/or $TiO_2$ and fillers such as quartz glass ceramic or glass powder, barium silicate glasses, barium fluorosilicate glasses, strontium silicate glasses, strontium borosilicate, Li/Al silicate glasses, barium glasses, calcium silicates, sodium aluminum silicates, fluoroaluminosilicate glasses, oxides of aluminum or silicon, zeolites, apatite, zirconium silicates, poorly soluble metal salts such as barium sulfate or calcium fluoride and X-ray-opaque fillers such as ytterbium fluoride.

In a preferred embodiment, a milling blank according to the invention contains barium-aluminum borosilicate glasses.

For better incorporation into the polymer matrix, the fillers can be organically surface-modified. By way of example, the surface treatment of the fillers with a silane may be mentioned. Particularly suitable as a coupling agent is methacryloxypropyltrimethoxysilane.

In a preferred embodiment, a milling blank according to the invention contains surface-treated barium-aluminum borosilicate glasses, preferably silanized barium-aluminum borosilicate glasses and most preferably barium-aluminum borosilicate glasses treated with methacryloxypropyltrimethoxysilane.

The milling blanks according to the invention can contain different silicic acids.

Preferably the milling blanks according to the invention contain nanoscale silicic acids. The nanoscale silicic acids are particles with an average particle size of not more than 80 nm. The production of the nanoscale silicic acids is effected in known manner, e.g. by flame pyrolysis, plasma methods, gas phase condensation, colloid techniques, precipitation methods, sol-gel methods, etc.

In a preferred configuration, the nanoscale silicic acids are present in non-agglomerated and non-aggregated form, preferably in monodisperse form.

In order to enable good incorporation of the nanoparticles into the polymer matrix of a radically curable dental composition, the surfaces of the nanoscale silicic acids are also organically surface-modified, i.e. their surfaces have organic structural elements. By way of example, the surface treatment of the fillers with a silane may be mentioned. As the coupling agent, methacryloxypropyltrimethoxysilane is also particularly suitable here.

In a preferred embodiment, a milling blank according to the invention contains surface-treated nanoscale, non-agglomerated and non-aggregated silicic acid particles with an average particle size of not more than 80 nm, preferably silanized nanoscale, non-agglomerated and non-aggregated particles with an average particle size of not more than 80 nm and most preferably nanoscale, non-agglomerated and non-aggregated silicic acid particles with an average particle size of not more than 80 nm treated with methacryloxypropyltrimethoxysilane.

Commercially available nanoscale, non-agglomerated and non-aggregated colloidal silica sols which can be used are for example traded under the name "NALCO COLLOIDAL SILICAS" (Nalco Chemical Co.), "Ludox colloidal silica" (Grace) or "Highlink OG" (Clariant).

In a preferred configuration, the filler content of the milling blank comprises a mixture of a first filler a2) in the form of non-agglomerated, non-aggregated, organically surface-modified nanoparticles with an average particle size less than 80 nm and a second filler a1) in the form of microparticles with an average particle size in the range from 0.4 μm to 5 μm. Through the combination of a2) nanoparticles and a1) microparticles in the polymer matrix a complete and uniform volume filling of the composite material is achieved.

The content of organically surface-modified nanoparticles in a milling blank according to the invention with an average particle size less than 80 nm is greater than 11.86 wt. % and less than 23 wt. %, based on the total composition. In our own studies, it was found that with a content of 11.86 wt. % or less or with a content of 23 wt. % and more of non-agglomerated and non-aggregated, organically surface-modified nanoparticles with an average particle size smaller than 80 nm the milling blank is no longer sufficiently swell-resistant.

Within the milling blank, the microparticles effect a largely uniform filling of the volume, wherein the remaining cavities between the microparticles are at least partially filled by the nanoparticles described above (component a2)). In connection with the present invention, microparticles are understood to be particles with an average particle size from 400 nm to 5 μm.

The microparticles of component a1) preferably have a bimodal particle size distribution. Microparticles with a bimodal particle size distribution are preferred since with them a more complete volume filling is achievable than with general use of microparticles of monomodal particle size distribution. In the presence of a bimodal particle size distribution, the particles of the fractions with the larger particle size effect a coarse filling of the volume, while the particles of the fraction with the smaller particle size will as far as possible fill the regions between the particles of the fractions with the larger particle size. The cavities still remaining are filled by nanoparticles as described above.

The milling blank according to the invention comprises a component a1), which a first microparticle fraction a1a), which each possess an average particle size in the range from 0.4 μm to 1 μm, preferably from 0.5 μm to 0.9 μm and a second microparticle fraction a1b), which each possess an average particle size in the range from 1.2 μm to 5.0 μm, preferably from 1.5 μm to 4.0 μm.

The ratio of the total mass of the first microparticle fraction to the total mass of the second microparticle fraction lies in the range from 1:1.5 to 1:8, preferably in the range from 1:2 to 1:5.

b) Radically Polymerizable Monomers/Radically Polymerized Monomers

The dental milling blank according to the invention comprises contents of radically polymerized monomers or radically polymerizable monomers of the polymerization product of a radically curable composition in a quantity of at most 16.7 wt. %, based on the total composition.

The radically polymerizable monomers of the polymerization product of a radically curable composition or the fractions of radically polymerized monomer can, without being limited thereto, be the (meth)acrylate monomers usually used in composite materials in dental chemistry.

In the patent literature, a large number of compounds are mentioned (for example also in DE 39 41 629 A1), all of which are diesters of acrylic or methacrylic acid and are suitable for use in a polymerization product of the present invention.

In a preferred embodiment, constituent (b) contains one or more monomers selected from the group consisting of ethylene glycol dimethacrylate (EGDMA), 1,6-hexanediol dimethacrylate (HDDMA), triethylene glycol dimethacrylate (TEGDMA), 1,10-decanediol dimethacrylate (DEDMA), 1,12-dodecanediol dimethacrylate (DODMA), ethoxylated bisphenol-A dimethacrylate and ethoxylated bisphenol-A dimethacrylate, wherein the bisphenol is reacted with 2 to 4 moles ethylene oxide and the intermediate product is then saturated with 2 moles methacrylic acid, polyethylene glycol dimethacrylate (PEGDMA), 7,7,9-trimethyl-4,13-dioxo-3,14-dioxa-5,12-diazahexadecane-1,16-dioxy dimethacrylate (UDMA), butanediol dimethacrylate, tetraethylene glycol dimethacrylate, neopentyl glycol dimethacrylate and bisphenol-A glycidyl methacrylate (bis-GMA).

Also usable are the corresponding dimethacrylates or diacrylates of dihydroxymethyltricyclo[$5.2.1.0^{2,6}$]decane, as described in the publications DE 1816823, DE 2419887, DE 2406557, DE 2931926, DE 3522005, DE 3522006, DE 3703120, DE 102005021332, DE 102005053775, DE 102006060983, DE 69935794 and DE 102007034457.

c) Initiators

The milling blank according to the invention is producible either by radiative curing (photochemically) and/or by chemical curing (redox reaction) and/or thermally. Thermal curing, which is for example brought about by peroxide decomposition, is preferred.

Examples of suitable photosensitizers are alpha-diketones, benzoin alkyl ethers, thioxanthones, benzophenones, acylphosphine oxides, acylgermanium compounds, acetophenones, ketals, titanocenes, sensitizing dyes, etc. The sensitizers can be used alone or in combination. Concrete examples of substances of the different classes are to be found for example in DE 10 2006 019 092 A1, or in DE 39 41 629 C2.

Examples of accelerators which are used together with the sensitizers are tertiary amines, secondary amines, barbituric acids, tin compounds, aldehydes and sulfur compounds. Concrete examples of substances of the different classes are to be found in DE 10 2006 019 092 or in DE 39 41 629 C2.

Further suitable initiators and initiator combinations are described in DE 601 16 142.

Suitable photoinitiators are characterized in that by absorption of light in the wavelength range from 300 nm to 700 nm, preferably from 350 nm to 600 nm and particularly preferably from 380 nm to 500 nm, optionally in combination with one or more coinitiators, they can effect the curing of a radically curable dental composition.

The absorption maximum of camphorquinone (CQ) lies at ca. 470 nm and thus in the blue light range. Camphorquinone (CQ) is one of the $PI_2$ initiators and is as a rule used together with a coinitiator.

A suitable catalyst system contains the combination of an alpha-diketone and an aromatic tertiary amine, and the combination of camphorquinone (CQ) and ethyl p-N,N-dimethylaminobenzoate (DABE) is preferred.

Also preferred is the further combination of the system "alpha-diketone/aromatic tertiary amine" with a phosphine oxide, in particular with phenyl-bis(2,4,6-trimethylbenzoyl) phosphine oxide and/or 2,4,6-trimethylbenzoyldiphenylphosphine oxide. Concerning the structure of suitable phosphine oxides, reference is made to the publications DE 38 01 511 C2, DE 10 2006 050 153 A1, EP 0 184 095 B1, DE 42 31 579 C2, EP 0 366 977 B1, U.S. Pat. No. 7,081,485 B2, DE 32 36 026 A1, US 2007/0027229 A1, EP 0 262 629 B1, EP 0 073 413, U.S. Pat. No. 7,148,382 B2, U.S. Pat. No. 5,761,169, DE 197 08 294 A1, EP 0 057 474, EP 0 047 902 A, EP 0 007 508, DE 600 29 481 T2, EP 0 980 682 B1, EP 0 948 955 B1, EP 1 236 459 B1 and EP 0 173 567 A2.

The phosphine oxides stated in these publications are particularly suitable as a photopolymerization initiator system alone or in combination with the system "alpha-diketone/amine".

Further suitable photoinitiators are described in J.-P. Fouassier, Photoinitiation, Photopolymerization and Photocuring, Hanser Publishers, Munich, Vienna, N.Y. 1995 and in J. F. Rabek (Ed.), Radiation Curing in Polymer Science and Technology, Vol. II, Elsevier Applied Science, London, N.Y. 1993.

Various initiators for chemical curing are known to those skilled in the art. By way of example, reference may be made to EP 1 720 506. Initiators for chemical curing are also described in the publications already mentioned above DE 10 2006 019 092 and in DE 39 41 629.

Preferred initiators for chemical curing are dibenzoyl peroxide, dilauroyl peroxide, in particular dibenzoyl peroxide in combination with amines such as N,N-dimethyl-p-toluidine, N,N-dihydroxyethyl-p-toluidine and structurally related amines.

Dual curing systems comprise a combination of photoinitiators and initiators for chemical curing.

As well as the oxidatively acting organic peroxide compounds, as redox systems barbituric acids or barbituric acid derivatives and malonylsulfamides can also be used.

Among the barbituric acid systems, the "Bredereck systems" are of great importance. Examples of suitable "Bredereck systems" and references to the relevant patent literature are to be found in EP 1 839 640 and in DE 1495520, WO 02/092021 or in WO 02/092023.

Instead of the barbituric acids, salts thereof can also be used. Examples of this are to be found in the following documents: EP 1 872 767, EP 2 070 506, EP 1 881 010, DE 10 2007 050 763, U.S. Pat. No. 6,288,138, DE 11 2006 001 049, U.S. Pat. No. 7,214,726 and EP 2 070 935.

Suitable malonylsulfamides are described in EP 0 059 451. Preferred compounds here are 2,6-dimethyl-4-isobutyl-malonylsulfamide, 2,6-diisobutyl-4-propylmalonylsulfamide, 2,6-dibutyl-4-propylmalonylsulfamide, 2,6-dimethyl-4-ethylmalonylsulfamide and 2,6-dioctyl-4-isobutylmalonylsulfamide.

Further, sulfur compounds in the oxidation state +2 or +4 such as sodium benzenesulfinate or sodium paratoluenesulfinate can be used.

To accelerate the curing, the polymerization can be performed in the presence of compounds of heavy metals such as Ce, Fe, Cu, Mn, Co, Sn or Zn, wherein copper compounds are particularly preferred. The heavy metal compounds are preferably used in the form of soluble organic compounds. Preferred copper compounds here are copper benzoate, copper acetate, copper ethylhexanoate, copper di(methacrylate), copper acetylacetonate and copper naphthenate.

If peroxides are heated, they decompose and form free radicals which are capable of starting the polymerization. The most widespread system for thermal polymerization is the use of dibenzoyl peroxide. Further thermal initiators are ketone peroxides, peroxyketals, hydroperoxides, dialkyl peroxides, diacyl peroxides, peroxy esters and peroxydicarbonates such as dicumyl peroxide, chlorobenzoyl peroxide, t-butyl perbenzoate, dilauroyl peroxide, cumene hydroperoxide and tert.-butylperont 3,5,5-trimethylhexanoate and azo compounds such as 2,2'-azobisisobutyronitrile, 2,2'-azobis-2,4-dimethylvaleronitrile, 2,2'-azobis-1-cyclohexanecarbonitrile or dimethyl 2,2'-azobisisobutyrate. Substances such as sodium or potassium persulfate also decompose thermally and are suitable compounds in this respect. These substances can be used singly or in mixtures with one another. For this, the radically curable compositions have merely to be heated to the decomposition temperature of the particular peroxide stated by the manufacturer. Advantageously, the radically curable compositions are heated to a temperature above the decomposition temperature and left there for some time, so that the polymerization product has time for relaxation. Those skilled in the art find the optimal temperature by successively increasing the temperature for the curing up to the point at which the polymerization product displays no significant improvements in the important parameters measured on it such as flexural strength, E modulus and water sorption.

Preferably the thermal curing is performed such that the radically curable composition is transferred into a block mold, where it is cured at temperatures from 80° C. to 150° C. and at a pressure from 100 to 300 bar.

d) Additives

A milling blank according to the invention in many cases comprises one or more further additive(s).

These additives can have various functions. Usual additives for use in dental materials are known to those skilled in the art, and depending on the desired function they will select the suitable additive(s). By way of example, typical additives and their functions are described below.

UV absorbers, which are able to absorb UV radiation for example through their conjugated double bond systems and aromatic rings, are in many cases a constituent of a milling blank according to the invention. Examples of UV absorbers are 2-hydroxy-4-methoxybenzophenone, phenyl salicylate, 3-(2'-hydroxy-5'-methylphenyl)benzotriazole or diethyl 2,5-dihydroxyterephthalate. The polymers contain these additives in order to ensure their color stability.

Since the teeth are to restored as realistically as possible, it is necessary to provide dental milling blanks in a great variety of coloring. As a rule, inorganic dyes and organic pigments in very small quantities are used for this purpose.

Further optional additives are dental medicaments and microbicides, preferably bactericides or fluorescent agents, which are also used in order to reproduce the natural appearance of teeth.

The present invention further relates to a process for the production of a milling blank for the production of permanent indirect restorations in the CAD/CAM process characterized in that it has a water sorption WSP of less than/equal to 18 µg/mm³, measured according to ISO 4049 and an E modulus E greater than/equal to 13 GPa, measured according to the ADA specification No. 27 and a quotient Q of WSP/E of less than 1.35 µg/(GPa×mm³), and preferably has a water sorption WSP of less than/equal to 15 µg/mm³, measured according to ISO 4049 and an E modulus E greater than/equal to 15 GPa, measured according to the ADA specification No. 27 and a quotient Q of WSP/E of less than 1 µg/(GPa×mm³) with the following steps:
  providing radically polymerizable monomers.
  providing inorganic fillers in a quantity of at least 83 wt. %, based on the total mass of the composition,
  providing a polymerization initiator,
  optionally providing additives,
  homogeneously mixing the components and
  polymerizing the mixture.

After for example a crown has been milled from the blank in the CAD/CAM process and the tooth core has been prepared, the dentist will preferably roughen the inner surface of the crown by sand-blasting, then clean and prime it. He will then apply and cure the bonding onto the core and finally fill a luting cement into the crown and place the latter on the core.

Preferably, the milling blanks are thus used as a constituent of a kit according to the invention. The present invention thus also relates to a kit, comprising
  milling blanks according to the invention in different colors,
  at least one primer,
  at least one dental adhesive,
  at least one luting cement and
  optionally further accessories such as brushes, polishing agents and mixing tips.

EXAMPLES

Abbreviations:
Bis-EMA2.6: Ethoxylated bisphenol A dimethacrylate with on average 2.6 ethylene oxide units
Bis-EMA4: Ethoxylated bisphenol A dimethacrylate with on average 4 ethylene oxide units
Bis-EMA6: Ethoxylated bisphenol A dimethacrylate with on average 6 ethylene oxide units
Bis-EMA10: Ethoxylated bisphenol A dimethacrylate with on average 10 ethylene oxide units
TCDDMA: Bis(methacryloyloxymethyhtricyclo[5.2.1.0$^{2,6}$]decane
UDMA: 7,7,9-Trimethyl-4,13-dioxo-3,14-dioxa-5,12-diazahexadecane-1,16-diyl dimethacrylate
TEGDMA: Triethylene glycol dimethacrylate
HDDMA: 1,6-Hexanediol dimethacrylate
DODMA: 1,12-Dodecanediol dimethacrylate
Dental glass 1: Barium-aluminum borosilicate glass (D50 0.8 µm/D25 0.5 µm/D75 1.0 µm)
Dental glass 2: Barium-aluminum borosilicate glass (D50 2.7 µm/D25 1.4 µm/D75 6.1 µm)
Dental glass 3: Barium-aluminum borosilicate glass (D50 1.1 µm/D25 0.7 µm/D75 1.4 µm)
Dental glass 4: Barium-aluminum borosilicate glass (D50 1.4 µm/D25 1.1 µm/D75 2.1 µm)
Dental glass 5: Barium-aluminum borosilicate glass (D50 1.4 µm/D25 0.8 µm/D75 2.9 µm)
Nano-SiO$_2$: Non-agglomerated, non-aggregated silicic acid (D50 40 nm)
BPO: Dibenzoyl peroxide Production of the Composite Pastes:

The individual components were weighed out according to the proportions stated in Tables 2 to 13, homogenized for 30 minutes at 50 rpm on a laboratory kneader (PC Laborsystem, Magden CH) and then degassed on the laboratory kneader for 15 minutes at 50 rpm and −0.85 bar.

Production of the Composite Blocks:

For the production of the composite blocks, the individual pastes were filled into molds (15 mm×15 mm×20 mm). The curing was effected isostatically at 250 bar and with the following temperature program (20° C.-2° C./min-120° C. (30 min)-5° C./min-20° C.).

Biaxial flexural strength (BBS): the biaxial flexural strength was determined analogously to DIN EN ISO 6872:2009 (7.3.3). For this, firstly cylinders with a diameter of 14 mm were ground from the composite blocks in a 5-axis milling machine (250i, imes-icore GmbH). From these cylinders, disks with a thickness of 1.2 mm were then produced with a high-speed saw (IsoMet 4000, Buehler), deburred, ground and polished. The samples were loaded with a traverse velocity of 1 mm/min up to fracture and the biaxial flexural strength calculated according to the formula given in 7.3.3.4. As the Poisson ratio, a value of 0.25 was used.

3-Point flexural strength (3PBS): the flexural strength was determined analogously to DIN EN ISO 6872:2009 (7.3.2) with span width of 12 mm and a support roller diameter of 2 mm. For this, from the composite blocks, test pieces with a breadth of 4 mm, a thickness of 1.2 mm and a length of 18 mm were produced with a high-speed saw (IsoMet 4000, Buehler), deburred, ground and polished. The samples were loaded with a traverse velocity of 1 mm/min up to fracture and the 3-point flexural strength calculated according to the formula given in 7.3.2.41.

Elastic modulus (E): The elastic modulus was determined analogously to the calculation in ADA Spec. No. 27:1993 (7.8.4.2) as the slope of the stress-strain curve of the 3-point flexural strength determination in the linear-elastic region.

$$E = \frac{3L}{4bh^3} \frac{\Delta F}{\Delta d}$$

L: span width
b: sample breadth
h: sample thickness
Δd: deformation in the linear-elastic region
ΔF: force change with a deformation Δd Water sorption ($W_{SP}$): the water sorption was determined analogously to DIN EN ISO 4049:2010 (7.12). For this, from the composite blocks, test pieces with a length of 14.7 mm, a breadth of 14.7 mm and a thickness of 0.5 mm were produced with a high-speed saw (IsoMet 4000, Buehler), deburred, ground and polished. The test pieces were dried to constant mass in the desiccator at 37° C. and the mass ($m_1$) precisely determined to within 0.1 mg, and the length, the breadth and the thickness to within 0.01 mm. Next, the test pieces were stored for 7 days at 37° C. in water. After 7 days, the test pieces were taken out, rinsed off with water, patted dry, swung backwards and forwards in air for 15 seconds and, 1 minute after removal from the water, precisely weighed to within 0.1 mg ($m_2$). After this weighing, the test pieces were dried to constant mass in the desiccator at 37°

C. and the mass ($m_3$) determined to within 0.1 mg. The water sorption was calculated according to the formula stated in 7.12.4.1.

Figure 3:
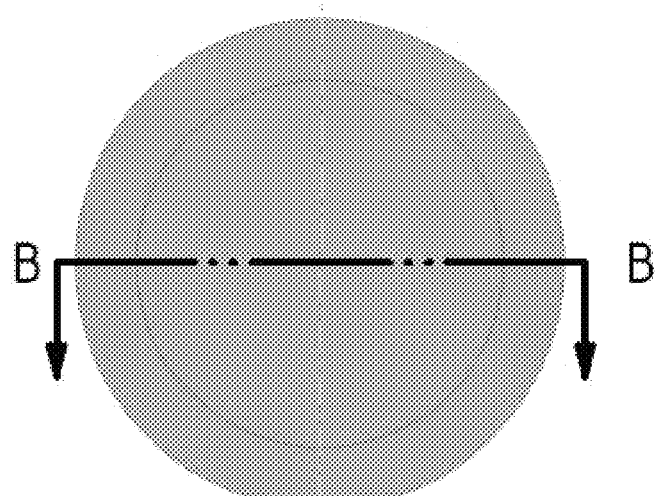
FIG. 3 shows the representation of an idealized crown for the determination of the linear swelling.
Figure 3:
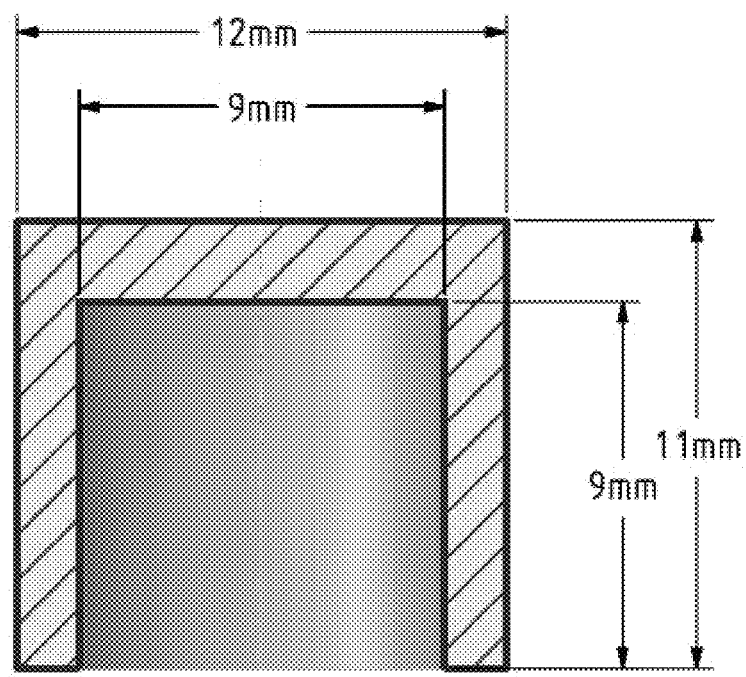

Linear swelling (LS): in a 5-axis milling machine (250i, imes-icore GmbH) idealized crowns were produced as test pieces from the composite blocks. These idealized crowns are hollow cylinders closed on one side (see FIG. 3). The height is 11 mm, the external diameter 12 mm and the internal diameter 9 mm. This corresponds to a wall thickness of 1.5 mm. The thickness of the cover plate is 2 mm. Next, the crowns were deburred, ground and polished. The test pieces were dried to constant mass in the desiccator at 37° C. and the internal diameter on the cylinder base determined precisely to within 0.001 mm at two mutually orthogonal points ($L_1$ and $L_2$). Next the test pieces were stored for 7 days at 37° C. in water. After 7 days, the test pieces were taken out, rinsed off with water, patted dry, swung backwards and forwards in air for 15 seconds and, 1 minute after removal from the water, the internal diameter on the cylinder base determined precisely to within 0.001 mm at the same two points as previously ($L_3$ and $L_4$). After the measurement, the test pieces were stored for a further 7 days at 37° C. in water. After this, the test pieces were taken out, dried as described above and the internal diameter again determined precisely to within 0.001 mm at the same two points as previously ($L_5$ and $L_6$). After the measurement, the test pieces were stored for a further 14 days at 37° C. in water. After this, the test pieces were taken out, dried as described above and the internal diameter again determined precisely to within 0.001 mm at the same two points as previously ($L_7$ and $L_8$). After the measurement, the test pieces were stored for a further 28 days at 37° C. in water. After this, the test pieces were taken out, dried as described above and the internal diameter again determined precisely to within 0.001 mm at the same two points as previously ($L_9$ and $L_{10}$). The linear swelling in % at the respective measurement times is obtained according to the following formulae.

$$LS_{1\ Week}\ [\%] = \frac{\frac{L_3+L_4}{2} - \frac{L_1+L_2}{2}}{\frac{L_1+L_2}{2}} \times 100\%$$

$$LS_{2\ Weeks}\ [\%] = \frac{\frac{L_5+L_6}{2} - \frac{L_1+L_2}{2}}{\frac{L_1+L_2}{2}} \times 100\%$$

$$LS_{4\ Weeks}\ [\%] = \frac{\frac{L_7+L_8}{2} - \frac{L_1+L_2}{2}}{\frac{L_1+L_2}{2}} \times 100\%$$

$$LS_{8\ Weeks}\ [\%] = \frac{\frac{L_9+L_{10}}{2} - \frac{L_1+L_2}{2}}{\frac{L_1+L_2}{2}} \times 100\%$$

Residue on ignition: for the determination of the residue on ignition, crucibles were heated for 10 hours at 150° C., allowed to cool to room temperature in the desiccator and then precisely weighed to within 0.1 mg ($m_1$). Ca. 1 g of the respective composite block was broken up, crushed and precisely weighed to within 0.1 mg in the crucible ($m_2$). This was heated at 575° C. for 3 hours in the muffle furnace, then the crucibles were allowed to cool to room temperature in the desiccator and the mass was then precisely determined to within 0.1 mg ($m_3$). The residue on ignition was calculated according to the following formula.

$$\text{residue on ignition}\ [\%] = \frac{m_3 - m_1}{m_2} \times 100\%$$

TABLE 1

|  | Lava Ultimate (3M Espe) | Cerasmart (GC) | Block HC (Shofu) | Crios (Coltene) |
|---|---|---|---|---|
| Filler content (manufacturer information) [%] | 80 |  |  | 70.7 |
| Residue on ignition [%] | 73 | 65 | 62 | 70 |
| Biaxial flexural strength [MPa] | 174 | 214 | 147 | 232 |
| 3-Point flexural strength [MPa] | 163 | 159 | 122 | 198 |
| E modulus [GPa] | 11.8 | 9.9 | 8.7 | 12.7 |
| WSP [µg/mm³] | 36 | 29 | 40 | 23 |
| WSP/E [µg/(GPa × mm³)] | 3.05 | 2.93 | 4.60 | 1.81 |
| LS (1 week) [%] | 0.23% | 0.19% | 0.27% | 0.15% |
| LS (2 weeks) [%] | 0.42% | 0.36% | 0.48% | 0.27% |
| LS (4 weeks) [%] | 0.51% | 0.42% | 0.60% | 0.34% |
| LS (8 weeks) [%] | 0.53% | 0.44% | 0.63% | 0.35% |

TABLE 2

| Example | | | 1 | 2 | 3 | 4 |
|---|---|---|---|---|---|---|
| Filler (a) | (a1a) | Dental glass 1 | 13.00 | 13.00 | 13.00 | 13.00 |
|  | (a1b) | Dental glass 2 Dental glass 3 Dental glass 4 Dental glass 5 | 57.50 | 57.50 | 57.50 | 57.50 |
|  | (a2) | Nano-SiO$_2$ (40 nm) | 15.00 | 15.00 | 15.00 | 15.00 |
|  | Total (a) |  | 85.50 | 85.50 | 85.50 | 85.50 |
| Monomers (b) | (b1a) | Bis-EMA2.6 Bis-EMA4 | 6.00 | 6.00 | 6.00 | 6.50 |
|  | (b1b) | Bis-EMA6 Bis-EMA10 |  |  |  |  |
|  | (b2) | TCDDMA | 3.75 | 5.00 | 2.50 | 3.50 |
|  |  | UDMA | 3.75 | 2.50 | 5.00 | 3.50 |
|  |  | HDDMA | 0.70 | 0.70 | 0.70 | 0.70 |
|  |  | DODMA |  |  |  |  |
|  |  | TEGDMA |  |  |  |  |
|  | Total (b) |  | 14.20 | 14.20 | 14.20 | 14.20 |
| Initiators (c) |  | BPO | 0.30 | 0.30 | 0.30 | 0.30 |
| Total |  |  | 100.00 | 100.00 | 100.00 | 100.00 |

TABLE 3

| Example | 1 | 2 | 3 | 4 |
|---|---|---|---|---|
| (a1a)/(a1b) | 0.23 | 0.23 | 0.23 | 0.23 |
| (a2)/[(a1a) + (a1b)] | 0.21 | 0.21 | 0.21 | 0.21 |
| (b1a)/(b) × 100% | 42.3% | 42.3% | 42.3% | 45.8% |
| Biaxial flexural strength [MPa] | 301 | 269 | 292 | 284 |

TABLE 3-continued

| Example | 1 | 2 | 3 | 4 |
|---|---|---|---|---|
| 3-Point flexural strength [MPa] | 274 | 241 | 266 | 259 |
| E modulus [GPa] | 18.3 | 15.8 | 18.6 | 16.4 |
| WSP [µg/mm$^3$] | 13 | 11 | 15 | 12 |
| WSP/E [µg/(GPa × mm$^3$)] | 0.71 | 0.70 | 0.81 | 0.73 |
| LS (1 week) [%] | 0.09% | 0.09% | 0.10% | 0.08% |
| LS (2 weeks) [%] | 0.15% | 0.14% | 0.16% | 0.13% |
| LS (4 weeks) [%] | 0.19% | 0.18% | 0.19% | 0.17% |
| LS (8 weeks) [%] | 0.19% | 0.19% | 0.20% | 0.18% |

TABLE 4

| | Example | | 5 | 6 | 7 | 8 |
|---|---|---|---|---|---|---|
| Filler (a) | (a1a) | Dental glass 1 | 13.00 | 13.00 | 13.00 | 13.00 |
| | (a1b) | Dental glass 2 | 57.50 | 57.50 | 57.50 | 57.50 |
| | | Dental glass 3 | | | | |
| | | Dental glass 4 | | | | |
| | | Dental glass 5 | | | | |
| | (a2) | Nano-SiO$_2$ (40 nm) | 15.00 | 15.00 | 15.00 | 15.00 |
| | Total (a) | | 85.50 | 85.50 | 85.50 | 85.50 |
| Monomers (b) | (b1a) | Bis-EMA2.6 | 7.00 | 5.80 | 6.00 | 6.00 |
| | | Bis-EMA4 | | | | |
| | (b1b) | Bis-EMA6 | | | | |
| | | Bis-EMA10 | | | | |
| | (b2) | TCDDMA | 3.25 | 3.85 | 3.75 | 3.75 |
| | | UDMA | 3.25 | 3.85 | 3.75 | 3.75 |
| | | HDDMA | 0.70 | 0.70 | | 0.70 |
| | | DODMA | | | 0.70 | |
| | | TEGDMA | | | | 0.70 |
| | Total (b) | | 14.20 | 14.20 | 14.20 | 14.20 |
| Initiators (c) | | BPO | 0.30 | 0.30 | 0.30 | 0.30 |
| Total | | | 100.00 | 100.00 | 100.00 | 100.00 |

TABLE 5

| Example | 5 | 6 | 7 | 8 |
|---|---|---|---|---|
| (a1a)/(a1b) | 0.23 | 0.23 | 0.23 | 0.23 |
| (a2)/[(a1a) + (a1b)] | 0.21 | 0.21 | 0.21 | 0.21 |
| (b1a)/(b) × 100% | 49.3% | 40.8% | 42.3% | 42.3% |
| Biaxial flexural strength [MPa] | 271 | 295 | 261 | 299 |
| 3-Point flexural strength [MPa] | 251 | 270 | 237 | 271 |
| E modulus [GPa] | 15.1 | 18.7 | 15.1 | 19.1 |
| WSP [µg/mm$^3$] | 13 | 15 | 11 | 14 |
| WSP/E [µg/(GPa × mm$^3$)] | 0.86 | 0.80 | 0.73 | 0.73 |
| LS (1 week) [%] | 0.09% | 0.09% | 0.05% | 0.07% |
| LS (2 weeks) [%] | 0.18% | 0.17% | 0.11% | 0.13% |
| LS (4 weeks) [%] | 0.21% | 0.20% | 0.17% | 0.16% |
| LS (8 weeks) [%] | 0.22% | 0.21% | 0.19% | 0.17% |

TABLE 6

| | Example | | 9 | 10 | 11 (Comparison) | 12 (Comparison) |
|---|---|---|---|---|---|---|
| Filler (a) | (a1a) | Dental glass 1 | | 13.00 | 13.00 | 13.00 |
| | (a1b) | Dental glass 2 | 70.50 | 57.50 | 57.50 | 57.50 |
| | | Dental glass 3 | | | | |
| | | Dental glass 4 | | | | |
| | | Dental glass 5 | | | | |
| | (a2) | Nano-SiO$_2$ (40 nm) | 15.00 | 15.00 | 15.00 | 15.00 |
| | Total (a) | | 85.50 | 85.50 | 85.50 | 85.50 |
| Monomers (b) | (b1a) | Bis-EMA2.6 | 6.00 | | | |
| | | Bis-EMA4 | | 6.00 | | |
| | (b1b) | Bis-EMA6 | | | 6.00 | |
| | | Bis-EMA10 | | | | 6.00 |
| | (b2) | TCDDMA | 3.75 | 3.75 | 3.75 | 3.75 |
| | | UDMA | 3.75 | 3.75 | 3.75 | 3.75 |
| | | HDDMA | | 0.70 | 0.70 | 0.70 |
| | | DODMA | | | | |
| | | TEGDMA | | | | |
| | Total (b) | | 14.20 | 14.20 | 14.20 | 14.20 |
| Initiators (c) | | BPO | 0.30 | 0.30 | 0.30 | 0.30 |
| Total | | | 100.00 | 100.00 | 100.00 | 100.00 |

TABLE 7

| Example | 9 | 10 | 11 (Comparison) | 12 (Comparison) |
|---|---|---|---|---|
| (a1a)/(a1b) | 0.00 | 0.23 | 0.23 | 0.23 |
| (a2)/[(a1a) + (a1b)] | 0.21 | 0.21 | 0.21 | 0.21 |
| (b1a)/(b) × 100% | 42.3% | 42.3% | 0.0% | 0.0% |
| Biaxial flexural strength [MPa] | 256 | 289 | 262 | 219 |
| 3-Point flexural strength [MPa] | 221 | 262 | 239 | 198 |
| E modulus [GPa] | 13.4 | 17.7 | 13.7 | 12.6 |
| WSP [µg/mm$^3$] | 18 | 15 | 19 | 26 |
| WSP/E [µg/(GPa × mm$^3$)] | 1.34 | 0.85 | 1.39 | 2.06 |
| LS (1 week) [%] | 0.13% | 0.10% | 0.15% | 0.17% |
| LS (2 weeks) [%] | 0.22% | 0.16% | 0.27% | 0.29% |
| LS (4 weeks) [%] | 0.28% | 0.21% | 0.31% | 0.36% |
| LS (8 weeks) [%] | 0.28% | 0.22% | 0.32% | 0.38% |

TABLE 8

| | Example | | 13 | 14 (Comparison) | 15 (Comparison) | 16 (Comparison) |
|---|---|---|---|---|---|---|
| Filler (a) | (a1a) | Dental glass 1 | 12.70 | 12.40 | 13.00 | 12.40 |
| | (a1b) | Dental glass 2 | 56.10 | 54.70 | 57.50 | 54.70 |
| | | Dental glass 3 | | | | |
| | | Dental glass 4 | | | | |
| | | Dental glass 5 | | | | |
| | (a2) | Nano-SiO$_2$ (40 nm) | 14.60 | 14.20 | 15.00 | 14.20 |
| | Total (a) | | 83.40 | 81.30 | 85.50 | 81.30 |
| Monomers (b) | (b1a) | Bis-EMA2.6 | 6.90 | 7.80 | 5.00 | 6.40 |
| | | Bis-EMA4 | | | | |
| | (b1b) | Bis-EMA6 | | | | |
| | | Bis-EMA10 | | | | |
| | (b2) | TCDDMA | 4.30 | 4.85 | 3.75 | 6.00 |
| | | UDMA | 4.30 | 4.85 | 3.75 | 6.00 |
| | | HDDMA | 0.80 | 0.90 | 1.70 | |
| | | DODMA | | | | |
| | | TEGDMA | | | | |
| | Total (b) | | 16.30 | 18.40 | 14.20 | 18.40 |
| Initiators (c) | | BPO | 0.30 | 0.30 | 0.30 | 0.30 |
| Total | | | 100.00 | 100.00 | 100.00 | 100.00 |

TABLE 9

| Example | 13 | 14 (Comparison) | 15 (Comparison) | 16 (Comparison) |
|---|---|---|---|---|
| (a1a)/(a1b) | 0.23 | 0.23 | 0.23 | 0.23 |
| (a2)/[(a1a) + (a1b)] | 0.21 | 0.21 | 0.21 | 0.21 |
| (b1a)/(b) × 100% | 42.3% | 42.4% | 35.2% | 34.8% |
| Biaxial flexural strength [MPa] | 266 | 201 | 189 | 203 |
| 3-Point flexural strength [MPa] | 240 | 175 | 169 | 177 |
| E modulus [GPa] | 16.7 | 13.7 | 11.8 | 12.1 |
| WSP [µg/mm$^3$] | 15 | 19 | 16 | 17 |
| WSP/E [µg/(GPa × mm$^3$)] | 0.90 | 1.39 | 1.36 | 1.40 |
| LS (1 week) [%] | 0.10% | 0.16% | 0.14% | 0.14% |
| LS (2 weeks) [%] | 0.17% | 0.26% | 0.24% | 0.26% |
| LS (4 weeks) [%] | 0.23% | 0.31% | 0.32% | 0.31% |
| LS (8 weeks) [%] | 0.23% | 0.31% | 0.32% | 0.32% |

TABLE 10

| Example | | | 17 (Comparison) | 18 (Comparison) | 19 | 20 (Comparison) |
|---|---|---|---|---|---|---|
| Filler (a) | (a1a) | Dental glass 1 | 13.00 | 12.40 | 12.70 | 12.40 |
| | (a1b) | Dental glass 2 | 57.50 | | | |
| | | Dental glass 3 | | 54.70 | | |
| | | Dental glass 4 | | | 56.10 | |
| | | Dental glass 5 | | | | 56.10 |
| | (a2) | Nano-SiO$_2$ (40 nm) | 15.00 | 14.20 | 14.60 | 14.60 |
| | | Total (a) | 85.50 | 81.30 | 83.40 | 83.40 |
| Monomers (b) | (b1a) | Bis-EMA2.6 | 7.50 | 7.80 | 6.90 | 6.90 |
| | | Bis-EMA4 | | | | |
| | (b1b) | Bis-EMA6 | | | | |
| | | Bis-EMA10 | | | | |
| | (b2) | TCDDMA | 3.00 | 4.85 | 4.30 | 4.30 |
| | | UDMA | 3.00 | 4.85 | 4.30 | 4.30 |
| | | HDDMA | 0.70 | 0.90 | 0.80 | 0.80 |
| | | DODMA | | | | |
| | | TEGDMA | | | | |
| | | Total (b) | 14.20 | 18.40 | 16.30 | 16.30 |
| Initiators (c) | | BPO | 0.30 | 0.30 | 0.30 | 0.30 |
| Total | | | 100.00 | 100.00 | 100.00 | 100.00 |

TABLE 11

| Example | 17 (Comparison) | 18 (Comparison) | 19 | 20 (Comparison) |
|---|---|---|---|---|
| (a1a)/(a1b) | 0.23 | 0.23 | 0.23 | 0.23 |
| (a2)/[(a1a) + (a1b)] | 0.21 | 0.21 | 0.21 | 0.21 |
| (b1a)/(b) × 100% | 52.8% | 42.4% | 42.3% | 42.3% |
| Biaxial flexural strength [MPa] | 198 | 213 | 265 | 231 |
| 3-Point flexural strength [MPa] | 177 | 194 | 242 | 211 |
| E modulus [GPa] | 11.0 | 14.4 | 14.7 | 12.5 |
| WSP [µg/mm$^3$] | 15 | 20 | 16 | 17 |
| WSP/E [µg/(GPa × mm$^3$)] | 1.36 | 1.39 | 1.09 | 1.36 |
| LS (1 week) [%] | 0.16% | 0.18% | 0.12% | 0.14% |
| LS (2 weeks) [%] | 0.25% | 0.27% | 0.19% | 0.23% |
| LS (4 weeks) [%] | 0.30% | 0.31% | 0.25% | 0.30% |
| LS (8 weeks) [%] | 0.31% | 0.31% | 0.26% | 0.31% |

TABLE 12

| Example | | | 21 (Comparison) | 22 (Comparison) | 23 (Comparison) | 24 (Comparison) |
|---|---|---|---|---|---|---|
| Filler (a) | (a1a) | Dental glass 1 | 35.25 | 7.00 | 10.00 | 13.92 |
| | (a1b) | Dental glass 2 | 35.25 | 60.10 | 44.20 | 61.58 |
| | | Dental glass 3 | | | | |
| | | Dental glass 4 | | | | |
| | | Dental glass 5 | | | | |
| | (a2) | Nano-SiO$_2$ (40 nm) | 15.00 | 14.20 | 25.00 | 10.00 |
| | | Total (a) | 85.50 | 81.30 | 79.20 | 85.50 |
| Monomers (b) | (b1a) | Bis-EMA2.6 | 6.00 | 7.80 | 8.70 | 6.00 |
| | | Bis-EMA4 | | | | |
| | (b1b) | Bis-EMA6 | | | | |
| | | Bis-EMA10 | | | | |

TABLE 12-continued

| Example | | | 21 (Comparison) | 22 (Comparison) | 23 (Comparison) | 24 (Comparison) |
|---|---|---|---|---|---|---|
| | (b2) | TCDDMA | 3.76 | 4.85 | 5.40 | 3.75 |
| | | UDMA | 3.75 | 4.85 | 5.40 | 3.75 |
| | | HDDMA | 0.70 | 0.90 | 1.00 | 0.70 |
| | | DODMA | | | | |
| | | TEGDMA | | | | |
| | Total (b) | | 14.20 | 18.40 | 20.50 | 14.20 |
| Initiators (c) | | BPO | 0.30 | 0.30 | 0.30 | 0.30 |
| Total | | | 100.00 | 100.00 | 100.00 | 100.00 |

TABLE 13

| Example | 21 (Comparison) | 22 (Comparison) | 23 (Comparison) | 24 (Comparison) |
|---|---|---|---|---|
| (a1a)/(a1b) | 1.00 | 0.12 | 0.23 | 0.23 |
| (a2)/[(a1a) + (a1b)] | 0.21 | 0.21 | 0.46 | 0.13 |
| (b1a)/(b) × 100% | 42.3% | 42.4% | 42.4% | 42.3% |
| Biaxial flexural strength [MPa] | 204 | 197 | 156 | 188 |
| 3-Point flexural strength [MPa] | 181 | 174 | 128 | 145 |
| E modulus [GPa] | 11.7 | 14.3 | 11.7 | 12.4 |
| WSP [µg/mm$^3$] | 19 | 21 | 31 | 21 |
| WSP/E [µg/(GPa × mm$^3$)] | 1.62 | 1.47 | 2.65 | 1.69 |
| LS (1 week) [%] | 0.19% | 0.20% | 0.23% | 0.21% |
| LS (2 weeks) [%] | 0.27% | 0.26% | 0.37% | 0.29% |
| LS (4 weeks) [%] | 0.32% | 0.31% | 0.43% | 0.34% |
| LS (8 weeks) [%] | 0.33% | 0.32% | 0.45% | 0.35% |

The invention claimed is:

1. A dental milling blank for the production of permanent indirect restorations in the CAD/CAM process, said dental milling blank having a water sorption WSP of less than or equal to 18 µg/mm$^3$ measured according to ISO 4049 and an elastic modulus E greater than or equal to 13 GPa, measured according to the ADA specification No. 27 and a quotient Q of WSP/E of less than 1.35 µg/(GPa×mm$^3$) and consists of the polymerization product of a radically curable dental composition, which comprises a) inorganic fillers, wherein the total mass of the inorganic fillers is at least 83 wt. %, based on the total mass of the composition, wherein the inorganic fillers a) comprise a1) a glass composition comprising a bimodal particle size distribution, and a2) non-aggregated and non-agglomerated silicic acid with an average particle size of not more than 80 nm, b) radically polymerizable monomers, c) one or more initiators for radically curing, wherein the glass composition a1) comprises a first glass composition a1a) with a D50 value from 0.4-1.0 µm, and a second glass composition a1b) with a D50 value from 1.2-5.0 µm.

2. The dental milling blank for the production of permanent indirect restorations in the CAD/CAM process as claimed in claim 1, wherein the dental milling blank has a water sorption WSP of less than/equal to 15 µg/mm$^3$, measured according to ISO 4049 and an elastic modulus E greater than/equal to 15 GPa, measured according to the ADA specification No. 27 and a quotient Q of WSP/E of less than 1 µg/(GPa×mm$^3$).

3. The dental milling blank for the production of permanent indirect restorations in the CAD/CAM process as claimed in claim 1, wherein the inorganic fillers a) are organically surface-coated.

4. The dental milling blank for the production of permanent indirect restorations in the CAD/CAM process as claimed in claim 3, wherein the inorganic fillers a) are silanized.

5. The dental milling blank for the production of permanent indirect restorations in the CAD/CAM process as claimed in claim 3, wherein the inorganic fillers a) are treated with methacryloxypropyltrimethoxysilane.

6. The dental milling blank for the production of permanent indirect restorations in the CAD/CAM process as claimed in one of claim 1, wherein the glass composition a1) is a barium-aluminum borosilicate composition.

7. The dental milling blank for the production of permanent indirect restorations in the CAD/CAM process as claimed in claim 1, wherein a mass ratio of a1a) to a1b) lies between 1:1.5 and 1:8.

8. The dental milling blank for the production of permanent indirect restorations in the CAD/CAM process as claimed in claim 1, wherein the glass composition a1) comprises the first glass composition a1a) with a D50 value from 0.5-0.9 µm, and the second glass composition a1b) with a D50 value from 1.5-4.0 µm.

9. The dental milling blank for the production of permanent indirect restorations in the CAD/CAM process as claimed in claim 8, wherein a mass ratio of a1a) to a1b) lies between 1:1.5 and 1:8.

10. The dental milling blank for the production of permanent indirect restorations in the CAD/CAM process as claimed in claim 1, wherein the content of the non-aggregated and non-agglomerated silicic acid with an average particle size of not more than 80 nm is greater than 11.86 wt. % and less than 23 wt. %, based on the total composition.

11. The dental milling blank for the production of permanent indirect restorations in the CAD/CAM process as claimed in claim 1, wherein the radically polymerizable monomers b) comprise bifunctional (meth)acrylates and wherein the proportion by weight of ethoxylated bisphenol-A dimethacrylate with an average degree of ethoxylation of 2 to 4 ethoxy groups per molecule is greater than 40% wt. % and less than 50 wt. % of b).

12. The dental milling blank for the production of permanent indirect restorations in the CAD/CAM process as claimed in claim 1, wherein the quantity of radically polymerizable monomers b) lies in a range of at most 16.7 wt. %, based on the total composition, and the quantity of one or more initiator(s) for radically curing c) lies in a range from 0.2 to 5 wt. %, based on the total composition, and the quantity of the additive or additives d) lies in a range from 0.001 wt. % to 2 wt. %, based on the total composition.

13. The dental milling blank for the production of permanent indirect restorations in the CAD/CAM process as claimed in claim 1, wherein the radically curable composition additionally comprises additives d).

14. A process for the production of a dental milling blank as claimed in claim 1 with the following steps:
providing the constituents a), b), and c),
homogeneously mixing the constituents and
curing the constituents.

15. A kit, comprising
several dental milling blanks as claimed in claim 10 in different colors,
at least one primer,
at least one dental adhesive,
at least one luting cement and
optionally further accessories such as brushes, polishing agents and mixing tips.

16. A dental milling blank for the production of permanent indirect restorations in the CAD/CAM process, said dental milling blank having a water sorption WSP of less than or equal to 18 μg/mm$^3$ measured according to ISO 4049 and an elastic modulus E greater than or equal to 13 GPa, measured according to the ADA specification No. 27 and a quotient Q of WSP/E of less than 1.35 μg/(GPa×mm$^3$) and consists of the polymerization product of a radically curable dental composition, which comprises
a) inorganic fillers, wherein the total mass of the inorganic fillers is at least 83 wt. %, based on the total mass of the composition, wherein the inorganic fillers a) comprise
a1) a glass composition comprising a bimodal particle size distribution, and
a2) non-aggregated and non-agglomerated silicic acid with an average particle size of not more than 80 nm,
b) radically polymerizable monomers,
c) one or more initiators for radically curing,
wherein the glass composition a1) comprises a first glass composition a1a) and a second glass composition a1b), wherein the D75 value of a1a) is smaller than the D25 value of a1b).

17. The dental milling blank for the production of permanent indirect restorations in the CAD/CAM process as claimed in claim 16, wherein the dental milling blank has a water sorption WSP of less than/equal to 15 μg/mm$^3$, measured according to ISO 4049 and an elastic modulus E greater than/equal to 15 GPa, measured according to the ADA specification No. 27 and a quotient Q of WSP/E of less than 1 μg/(GPa×mm$^3$).

18. The dental milling blank for the production of permanent indirect restorations in the CAD/CAM process as claimed in claim 16, wherein a mass ratio of a1a) to a1b) lies between 1:1.5 and 1:8.

19. The dental milling blank for the production of permanent indirect restorations in the CAD/CAM process as claimed in claim 16, wherein a mass ratio of a2) to the sum of a1a) and a1b) lies between 1:3 and 1:6.

20. The dental milling blank for the production of permanent indirect restorations in the CAD/CAM process as claimed in claim 16, wherein a ratio of the average particle she of first glass composition a1a) to the average particle size of second glass composition a1b) lies in the range from 1:1.5 to 1:10.

* * * * *